United States Patent [19]

Dalbøge et al.

[11] Patent Number: 5,691,169
[45] Date of Patent: *Nov. 25, 1997

[54] PROCESS FOR PREPARING A DESIRED PROTEIN

[75] Inventors: Henrik Dalbøge, Virum; John Pedersen, Kokkedal; Thorkild Christensen, Allerød; Jørli Winnie Ringsted, Brøndby; Torben Ehlern Jessen, Holbaek, all of Denmark

[73] Assignee: Novo Nordisk A/S, Denmark

[*] Notice: The term of this patent shall not extend beyond the expiration date of Pat. No. 5,518,697.

[21] Appl. No.: 402,455

[22] Filed: Mar. 10, 1995

Related U.S. Application Data

[63] Continuation of Ser. No. 372,692, Jan. 13, 1995, Pat. No. 5,618,597, which is a continuation of Ser. No. 959,856, Nov. 12, 1992, abandoned, which is a continuation of Ser. No. 759,106, Sep. 6, 1991, abandoned, which is a continuation of Ser. No. 215,602, Jul. 1, 1988, abandoned, which is a continuation-in-part of Ser. No. 910,230, Oct. 2, 1986, abandoned, which is a continuation-in-part of Ser. No. 640,081, filed as PCT/DK83/00118 DEc. 9, 1983, abandoned.

[30] Foreign Application Priority Data

Dec. 10, 1982 [DK] Denmark ................... 5493/82
Feb. 7, 1985 [DK] Denmark ................... 556/85

[51] Int. Cl.$^6$ .............. C12P 21/06; C12P 19/56; C12N 1/20; C07K 14/61
[52] U.S. Cl. ............. 435/69.7; 435/69.4; 435/320.1; 435/252.3; 435/252.33; 435/325; 435/78; 530/399; 530/303
[58] Field of Search ................ 435/69.4, 69.7, 435/325, 78, 320.1, 252.3, 252.33; 530/399, 303

[56] References Cited

U.S. PATENT DOCUMENTS

| | | | |
|---|---|---|---|
| 4,543,329 | 9/1985 | Daum et al. | 435/69 |
| 4,745,069 | 5/1988 | Mayne et al. | 435/320 |
| 4,755,465 | 7/1988 | Grey et al. | 435/70 |
| 4,769,326 | 9/1988 | Rutter et al. | 435/68 |
| 4,775,622 | 10/1988 | Hitzeman et al. | 435/68 |

FOREIGN PATENT DOCUMENTS 0089626  9/1983  European Pat. Off. .

OTHER PUBLICATIONS

Light et al. 1980. Analytical Biochem. 106:199–206.
Stryer et al 1981 Biochemistry 2nd Ed. W.H. Freeman & Co. San Francisco, p. 26.
BMAs Patent; Trademark, & Copyright Journal 53: 419–421 1997.
Goeddel et al 1979 Nature : 281:544–548.
Callahan et al 1972 Fed. Proc. 31 :1105–1113.

*Primary Examiner*—Karen C. Carlson
*Attorney, Agent, or Firm*—Albert L. Jacobs, Jr.; Steve T. Zelson; Cherly Agris

[57] ABSTRACT

A desired protein having the formula:

A-B-C-P wherein
a) A is Lys or Arg, and B and C are arbitrary amino acids, or
b) A is an arbitrary amino acid different from Pro, Lys and Arg, and B and/or C is Pro,
is produced from a biosynthetically formed amino acid extended protein having the formula:

X-A-B-C-P wherein A, B, C and P are as defined above, and X is an amino acid sequence with an even number of amino acids, of which the first one, seen from the N-terminal end, is different from Lys and Arg, all other uneven amino acids are different from Pro, Lys and Arg, and all even amino acids are different from Pro, by reaction with the enzyme dipeptidyl aminopeptidase (DAP I). The desired protein is obtained in a pure state. Thus, e.g. hGH without content of Met-hGH may be produced by the process.

44 Claims, No Drawings

PROCESS FOR PREPARING A DESIRED PROTEIN

This application is a continuation of Ser. No. 372,692, filed Jan. 13, 1995, now U.S. Pat. No. 5,618,597, which is a continuation of Ser. No. 959,856, Nov. 12, 1992, abandoned, which is a continuation of Ser. No. 759,106, Sep. 6, 1991, abandoned, which is a continuation of Ser. No. 215,602, Jul. 1, 1988, abandoned, which is a continuation-in-part of Ser. No. 910,230, Oct. 2, 1986, abandoned, which is a continuation-in-part of Ser. No. 640,081, filed Aug. 8, 1984, filed as PCT/DK83/00118, Dec. 9, 1983, now abandoned.

The present invention concerns a process for preparing a desired protein having the formula stated in the introductory portion of claim 1.

It is known from the U.S. Pat. No. 4,342,832 to produce biosynthetic hGH by fermentation of a recombinant host cell, in particular *E. coli*, which codes for hGH with associated methionine. However, this known process results in hGH whose N terminus has attached to it the amino acid methionine which is not present in ripe hGH.

Owing to the risk of antigenic reactions and other side effects in the use of a growth hormone which is not quite identical with hGH, it is inexpedient to use biosynthetic Met-hGH.

Accordingly, there is a great need for a process which enables production of biosynthetic hGH with a correct amino acid sequence. A solution to this problem has been proposed by U.S. patent application Ser. No. 488 232 (DK Patent Application 2046/84), which concerns a process for producing hGH from pre-hGH in a recombinant prokaryotic microorganism, such as *Pseudomonas aeruginosa* or *E. coli*.

The use of *Ps. aeruginosa* for the production of hGH without methionine for therapeutic use, however, is vitiated by the risk that this bacterium and many other Pseodomonas bacteria, which are potentially pathogenic, synthesize toxic toxins which are problematic.

The expression of pre-hGH followed by proteolytic cleavage to obtain ripe hGH in *E. coli* (which is not pathogenic) is indicated in the DK Patent Application 2046/84, but it is not documented in that specification that the proteolytic cleavage unambiguously leads to the formation of ripe hGH, i.e. with a correct amino acid sequence.

As mentioned above; risks may be involved in using Met-hGH. Though methods have been proposed for enzymatic cleavage of the methionine group by means of aminopeptidases, the problem would not be solved by this because the known enzymatic processes of this type do not lead to a 100% conversion. A mixture of hGH and Met-hGH would occur, which cannot be separated completely by conventional preparative purification processes.

The present invention is based on the finding that the enzyme dipeptidyl aminopeptidase I (DAP I) or cathepsin C (EC(3,4,14,1)) is suitable for cleaving an N-terminal amino acid sequence with an even number of amino acids to form a desired protein having the formula:

A-B-C-P wherein a) A is Lys or Arg, and B and C are arbitrary amino acids, or b) A is an arbitrary amino acid different from Pro, Lys and Arg, and B and/or C is Pro, and P is in both cases the residual amino acid sequence in the desired protein.

Thus, DAP I has been found suitable not only for production of hGH in which the three first amino acids are Phe-Pro-Thr, but proteins in general which satisfy the conditions of the sequence A-B-C-P.

Thus, the process of the invention is characterized in that a biosynthetically formed amino terminal extended protein having the formula:

X-A-B-C-P, wherein A, B, C and P are as defined above, and X is an amino acid sequence having an even number of amino acids, of which the first one, seen from the N-terminal end, is different from Lys and Arg, all other uneven amino acids are different from Pro, Lys and Arg, and all even amino acids are different from Pro, is reacted with the enzyme dipeptidyl aminopeptidase I (DAP I).

Examples of proteins which may be produced by the process of the invention are the following:

| Name | Origin | N-terminal sequence |
|---|---|---|
| Proteins with lysine in the first site | | |
| Cholecystokinin | Porcine | Lys—Ala—Pro— |
| Neurotoxin I | Scorpion | Lys—Asp—Gly— |
| Penicillinase | Staphylococcus Aureus | Lys—Glu—Leu— |
| Ribonuclease | Bovine | Lys—Glu—Ser— |
| Proparathyrin | Human | Lys—Ser—Val— |
| Lactalbumin | Human | Lys—Glu—Phe— |
| Kallidin II | Human | Lys—Arg—Pro— |
| Purothionine A-I | Wheat | Lys—Ser—Cys— |
| Viscotoxin A3 | Eru. Mistelten | Lys—Ser—Cys— |
| Lysozyme | Human | Lys—Val—Phe |
| Proteins with arginine in the first site | | |
| Beta Casein | Bovine | Arg—Glu—Leu— |
| Posterior Pituitary Peptide | Bovine | Arg—Gly—Gln— |
| Serum Albumin Precursor | Bovine | Arg—Gly—Val— |
| Long Neurotoxin I | Black Mamba | Arg—Thr—Cys— |
| Tuberculin-Active Protein | Mycobacterium Tuberculosis | Arg—Leu—Leu |
| Bradykinin (Kallidin I) | Bovine | Arg—Pro—Pro |
| Amyloid Protein AA | Human | Arg—Ser—Phe— |
| Proteins with proline in the second site | | |
| Choriogonadotropin | Human | Ala—Pro—Asx— |
| Follitropin (α-chain) | Human | Ala—Pro—Asp— |
| Pancreatic Hormone | Bovine | Ala—Pro—Lys— |
| Aspartate Aminotransferase | Porcine | Ala—Pro—Pro— |
| Plasminogen | Human | Glu—Pro—Leu— |
| Insulin-like Growth Hormone | Human | Gly—Pro—Glu— |
| Prealbumin | Human | Gly—Pro—Thr— |
| Prolactin | Porcine | Leu—Pro—Ile— |
| Lipid-binding Protein C-I | Human | Thr—Pro—Asp— |
| Cholera Enterotoxin (β-chain) | Vibrio Cholerae | Thr—Pro—Glu— |
| Prolactin | Bovine | Thr—Pro—Val— |
| Lymphotoxin | Human | Lys—Pro—Gly— |
| Interleukin-2 | Human | Ala—Pro1—Pro— |
| Somatotropin | Bovine | Phe—Pro—Pro— |
| Proteins with proline in the third site | | |
| Neurocarzinostatin | Streptomyces Carzinostaticus | Ala—Ala—Pro— |
| Carbonic Anhydrase B | Human | Ala—Ser—Pro— |
| Toxin II | Sea Anemone | Gly—Val—Pro— |
| Allergin RA5 | Wormwood | Leu—Val—Pro— |
| Lac Repressor | *E. coli* | Met—Lys—Pro— |

| Name | Origin | N-terminal sequence |
|---|---|---|
| Alcohol Dehydrogenase | Yeast | Ser—Ile—Pro— |
| Orosomukoid | Human | Glx—Ile—Pro— |
| Interleukin-1 | Murin | Ser—Ala—Pro— |

Examples of starting materials which may be cleaved with DAP I are the following:

| | | |
|---|---|---|
| Met—Glu—Ala—Glu | hGH | |
| Met—Phe—Glu—Glu | hGH | to obtain hGH |
| Met—Thr—Glu—Glu | hGH | (proline in the second site) |
| Met—Glu—Glu—Glu | hGH | |
| Ala—Ala—Glu—Glu | hGH | |
| Met—Phe— | Glu—hGH | |
| Met—Leu— | Glu—hGH | to obtain Glu—hGH |
| Ala—Glu | Glu—hGH | (proline in the third site) |
| Met—Ala— | Glu—hGH | |

The present process is thus suitable for production of biosynthetic proteins, such as hGH having attached to it a pre-sequence which can be cleaved enzymatically in a high yield, and which gives products by the enzymatic cleavage which may be separated satisfactorily by known purification methods, such as ion exchange.

Examples of suitable amino terminal extensions which may be cleaved by means of DAP I are those in which the last amino acid in the amino acid sequence X, before A, is an amino acid with a charged side chain, such as Glu or Asp.

These amino terminal extensions may be obtained by fermentation in a suitable substrate of a microorganism which is transformed with a plasmid coding for the desired extended protein.

After expression, the methionine residue is optionally cleaved enzymatically in the microorganism so that the recovered protein is attached to the desired amino terminal extension with an even number of amino acids which may be cleaved selectively and in a high yield. Isolation of the resulting protein takes place in a manner known per se, e.g. by chromatographic methods.

By selecting an amino extension which contains at least one amino acid with a charged side chain, such as a carboxyl group, it is possible to perform the separation and the purification of amino terminal extended protein from the ripe protein.

At least one of the charged amino acids may be attached directly to the N-terminal end of the protein because it may then be observed whether the entire amino terminal extension has been cleaved. This is particularly important when the microorganism in vivo only partly cleaves the N-terminal methionine residue.

It is most expedient that an amino acid with charged side chains in the amino terminal extension to the protein is either exclusively positively or negatively charged. This prevents amino terminal extended protein, partly enzymatically converted amino terminal extended protein and authentic protein from having the same net charge at any time.

In hGH, slight deamidation of certain Gln and Ash residues takes place, i.e. Gln and Ash are converted to Glu and Asp, respectively—i.e. amino acids with negatively charged side chains. For this reason it will therefore be most expedient that the charged amino acid in the amino terminal extension are the negatively charged Glu and/or Asp, because this avoids the situation of one or more deamidations in hGH neutralizing the positive charge/charges present in the extension. Such neutralization of charges will make it impossible to separate possibly unreacted deamided amino terminal extended hGH by ion exchange from the enzymatically formed hGH.

Examples of particularly suitable amino terminal extensions which may be cleaved with DAP I are 1. Met-Glu-Ala-Glu
2. (Ala-Glu)$_r$, wherein r is an integer from 1 to 12
3. Met-Phe-Glu-Glu
4. Thr-Glu-Ala-Glu
5. Met-Asp-Ala-Asp
6. Met-Glu-Ala-Asp These and other suitable amino terminal extensions may be obtained by fermenting in a suitable substrate a microorganism transformed with a plasmid, which codes for the desired protein with these attached amino terminal extensions.

In some specific pre-sequences, methionine, which is the N-terminal amino acid in all proteins formed in *E. coli*, is cleaved enzymatically in the microorganism after expression of the protein. This results e.g. in the above-mentioned amino terminal extended proteins.

These proteins are purified by conventional purification methods. The amino terminal extension is cleaved selectively and in a high yield. The formed protein may then easily be separated from any residues of partly converted amino terminal extended protein by known chromatographic methods.

The process of the invention will be illustrated more fully below by means of some working examples.

EXAMPLE 1

Preparation of hGH by means of DAP I

A cloned DNA sequence which codes for a protein having an amino acid sequence like human growth hormone, hGH (191 amino acid residues, the first four amino acids of which are Phe-Pro-Thr-Ile) is coupled with the following synthetically produced, dual-stranded DNA sequence so that the 3' end of the + strand is coupled to the +5' end of the above-mentioned gene, and the 5' end of the synthetic DNA sequence strand is coupled to the 3' end of the above-mentioned gene by blunt end ligature

```
+5'  CGATG  GCT  GAA
 -3'    TAC  CGA  CTT
``` where the 2 first nucleotides in the + strand are a ClaI restriction site overhang, and the following nucleotide sequences code for the amino acids Met-Ala-Glu-.

The above-mentioned gene is introduced by ordinary gene cloning techniques into an expression plasmid containing a fused Trp-Lac promotor as well as the SD sequence AGGA. This structure expresses Met-Ala-Glu-hGH.

This plasmid structure is then introduced into an *E. coli* cell by prior art techniques. A suitable clone containing the above-mentioned structure is isolated and cultivated in a 5:1 scale. The cells were harvested by centrifugation and are suspended in a small volume and lyzated using a so-called "French press".

The expected fusion protein could be demonstrated in the above-mentioned bacterial extract by immunological methods using hGH antibodies, corresponding to a concentration of 200 mg/l in the culture medium.

The fusion protein is purified conventionally by anion exhange, ammonium sulfate precipitation and hydrophobic chromatography.

The purified Met-Ala-Glu-hGH was evaluated to be more than 99% pure, evaluated by SDS electrophoresis.

An amino terminal sequence determination showed that the purified hGh material had the sequence Ala-Glu-hGH, which means that Met has been cleaved by an *E. coli* enzyme.

100 mg of AE-hGH in 10 mM Tris-Cl. pH 4.2 (1.5 mg/ml) were admixed with 5 mg of DAP I (3,4,14,1).

The reaction mixture was then incubated at 40° C. After 4½ hours the mixture was cooled to 4° C. The cooled reaction mixture was then fractionated by anion exchange, and following this the main peak (hGH product) was isolated. The yield was 90%.

The hGH product was shown to be more than 99% pure, evaluated by SDS electrophoresis. An amino terminal determination (Edman degradation) showed that the amino terminal sequence of the hGH product was Phe-Pro-Thr-Ile-Pro-, i.e. as for authentic hGH.

The biological activity of the hGH product was determined by a tibia test and was found to be 2.5 IU/mg, which is also the case with authentic hGH.

EXAMPLE 2

Preparation of hGH from Met-Glu-Ala-Glu-hGH with Dipeptidyl Aminopeptidase I, (DAP I)

Met-Glu-Ala-Glu-hGh is produced by gene techniques in principle as described in example 1. Met-Glu-Ala-Glu-hGH is purified from the fermentation product by anion exchange and hydrophobic interaction chromatography.

The purified Met-Glu-Ala-Glu-hGh was evaluated to be more than 99% pure by ion exchange and SDS electrophoresis.

An amino terminal sequence determination showed that the purified hGH had the sequence Met-Glu-Ala-Glu-Phe-Pro-Thr-Ile-Pro-Leu, where the last six amino acids correspond to the N-terminus in hGH. 200 ml of Met-Glu-Ala-Glu- hGH (2.0 mg/ml) in 20 mM Tris, 10 mM citric acid, 25 mM Nacl, pH 5.2 were admixed with 10,000 mU (corresponding to 3.3 mg) dipeptidyl aminopeptidase I (E.C. 3,4,14,1) from Boehringer Mannheim. Other makes may be used as well. The pH value is optionally readjusted to 4.2.

The reaction mixture was then incubated at 40° C. for 60 minutes, resulting in a more than 98% conversion of Met-Glu-Ala-Glu-hGh to hGH. The reaction mixture was cooled to 4° C. after completed reaction. The further purification comprises isoprecipitation, gel filtration and an anion exchange.

The hGH product was shown to be more than 99% pure evaluated by IE-HPLC and SDS electrophoresis. An amino terminal sequence determination by Edman degradation showed that the amino terminal sequence of the HGH product was Phe-Pro-Thr-Ile-Pro-Leu, i.e. as for authentic hGH.

The biological activity of the hGH product was determined by a tibia test and was found to be equipotent with pituitary hGH.

EXAMPLE 3

Preparation of hGH from Met-Phe-Glu-Glu-hGH with Dipeptidyl Aminopeptidase I

Met-Phe-Glu-Glu-hGh is produced by gene techniques in principle as described in example 1. Met-Phe-Glu-Glu-hGH is purified from the fermentation product by anion exchange and hydrophobic interaction chromatography.

The purified Met-Phe-Glu-Glu-hGH was evaluated to be more than 99% pure by IE-HPLC and SDS electrophoresis.

An amino terminal sequence determination showed that the purified hGH product had the sequence Met-Phe-Glu-Glu-Phr-Thr-Ile-Pro-Leu, where the last six amino acids correspond to the N-terminus in hGH.

100 ml of Met-Phe-Glu-Glu-hGH (1.5 mg/ml) in 20 mM Tris, 10 mM citric acid, 25 mM NaCl, 1 mM L-Cysteine pH 4.2 were admixed with 15,000 mU (corresponding to 5.0 mg) aminopeptidase I (E.C. 3,4,14,1) from Boehringer Mannheim. Other makes may be used as well. The pH value is optionally readjusted to 4.2.

The reaction mixture was then incubated at 40° C. for 60 minutes, resulting in a more than 98% conversion of Met-Phe-Glu-Glu-hGH to hGH. The reaction mixture was cooled to 4° C. after completed reaction. The further purification comprises isoprecipitation, gel filtration and an anion exchange.

The hGH product was shown to be more than 99% pure evaluated by IE-HPLC and SDS electrophoresis. An amino terminal sequence determination by Edman degradation showed that the amino terminal sequence of the hGH product was Phe-Pro-Thr-Ile-Pro-Leu, i.e. as for authentic hGH.

The biological activity of the hGH product was determined by a tibia test and was found to be equipotent with pituitary hGH.

EXAMPLE 4

Preparation of hGH from Ala-Glu-Ala-Glu-hGH with Dipeptidyl Aminopeptidase I

Met-Ala-Glu-Ala-Glu-hGH is produced by gene techniques in principle as described in example 1. Met is cleaved in vivo so that the protein formed by fermentation is Ala-Glu-Ala-Glu-hGH. This is purified conventionally by anion exchange and hydrophobic interaction chromatography.

The purified Ala-Glu-Ala-Glu-hGH was evaluated to be more than 99% pure by IE-HPLC and SDS electrophoresis.

An amino terminal sequence determination showed that the purified hGH product had the sequence Ala-Glu-Ala-Glu-Phe-Pro-Thr-Ile-Leu-Pro-Leu, where the last six amino acids correspond to the N-terminus in hGH.

100 ml of Ala-Glu-Ala-Glu-hGH (2.0 mg/ml) in 20 mM Tris, 10 mM citric acid, 25 mM NaCl, pH 4.2 were admixed with 20,000 mU (corresponding to 6.7 mg) Dipeptidyl Aminopeptidase I (E.C. 3,4,14,1) from Boehringer Mannheim. Other makes may be used as well. The pH value is optionally readjusted to 4.2.

The reaction mixture was then incubated at 40° C. for 60 minutes, resulting in a more than 98% conversion of Ala-Glu-Ala-Glu-hGH to hGH. The reaction mixture was cooled to 4° C. after completed reaction. The further purification comprises isoprecipitation, gel filtration and an anion exchange.

The hGH product was shown to be more than 99% pure evaluated by IE-HPLC and SDS electrophoresis. An amino terminal sequence determination by Edman degradation showed that the amino terminal sequence of the hGH product was Phe-Pro-Thr-Ile-Pro-Leu, i.e. as for authentic hGH.

EXAMPLE 5

Preparation of ILIβ from Met-Glu-Ala-Glu-ILIβ

Biosynthetically produced Met-Glu-Ala-Glu-ILIβ was purified and isolated by chromatography, and the eluate was admixed with 0.38 unit of DAP I (from Boehringer Mannheim, called cathepsin C, 21.9 IU/ml) per m g of protein, calculated on the basis of E (280, 0.1%)=0.6. The reaction mixture was left to stand for 45 min. at 37° C. The solution was dialyzed against 20 mM Na-citrate, 2 mM EDTA, pH=4.0 at 4° C. for 18 hours.

The dialysate was applied to an FF-Q Sepharose CL6B column in Tris-Cl pH=8.0 with an NaCl gradient to 0.2M.

The ILIβ fraction was concentrated by ultrafiltration with a 10 ml Nova cell to a volume of 2.0 ml (c=7.0 mg per ml). The pooled concentrate was applied to a Sephacryl column in 0.5M Na-acetate, pH=3.5.

The product was characterized by amino acid analysis and N-terminal sequence analysis. The sequence was shown to be identical with the first 42 N-terminal amino acids in authentic ILIβ.

EXAMPLE 6

Preparation of human lysozyme (hLZ)

Usual biotechnological methods are used for preparation of the gene for the protein MFEE-hLZ, where hLZ has the amino acid sequence:

| 1   | K | V | F | E | R | C | E | L | A | R | T | L | K | R | L | G | M | D | G | Y | R | G | I | S | L | A | N | W | M | C |
|-----|---|---|---|---|---|---|---|---|---|---|---|---|---|---|---|---|---|---|---|---|---|---|---|---|---|---|---|---|---|---|
| 31  | L | A | K | W | E | S | G | Y | N | T | R | A | T | N | Y | N | A | G | D | R | S | T | D | Y | G | I | F | Q | I | N |
| 61  | S | R | Y | W | C | N | D | G | K | T | P | G | A | V | N | A | C | H | L | S | C | S | A | L | L | Q | D | N | I | A |
| 91  | D | A | V | A | C | A | K | R | V | V | R | D | P | Q | G | I | R | A | W | V | A | W | R | N | R | C | Q | N | R | D |
| 121 | V | R | Q | Y | V | Q | G | C | G | V | * |   |   |   |   |   |   |   |   |   |   |   |   |   |   |   |   |   |   |   |

The gene is introduced into a suitable expression system and cultivated to form MFEE-hLZ. This protein was purified and treated with DAP I under the conditions stated in example 1. Thereby, authentic pure human lysozyme is isolated.

EXAMPLE 7

Preparation of IGF-1

Usual biotechnological methods are used for the preparation of a plasmid which codes for an extended human insulin-like growth factor 1 having the formula Met-Phe-Glu-Glu-IGF-1, where the sequence IGF has the following structure:

```
1                                         10
Gly—Pro—Glu—Thr—Leu—Cys—Gly—Ala—Glu—Leu—Val—Asp

20
Ala—Leu—Gln—Phe—Val—Cys—Gly—Asp—Arg—Gly—Phe—Tyr—Phe—

30
Asn—Lys—Pro—Thr—Gly—Tyr—Gly—Ser—Ser—Ser—Arg—Arg—Ala—

40                                   50
Pro—Gln—Thr—Gly—Ile—Val—Asp—Glu—Cys—Cys—Phr—Arg—Ser—

60
Cys—Asp—Leu—Arg—Arg—Leu—Glu—Met—Tyr—Cys—Ala—Pro—Leu—

70
Lys—Pro—Ala—Lys—Ser—Ala
```

The plasmid is introduced into *E. coli*, which is cultivated under usual conditions. The formed fusion product is isolated and purified in a known manner and treated with the enzyme DAP I to form authentic human IGF-1.

EXAMPLE 8

Preparation of bovine growth factor, bGH

Usual biotechnological methods are used for the preparation of plasmid which codes for an extended bovine growth hormone having the formula MFEE-bGH, where the sequence bGH has the following structure:

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| 1 | A | F | P | A | M | S | L | S | G | L | F | A | N | A | V | L | R | A | Q | H | L | H | Q | L | A | A | D | T | F | K |
| 30 | E | F | E | R | T | Y | I | P | E | G | Q | R | Y | S | I | Q | N | T | Q | V | A | F | C | F | S | E | T | I | P | A |
| 60 | P | T | G | K | N | E | A | Q | Q | K | S | D | L | E | L | L | R | I | S | L | L | L | I | Q | S | W | L | G | P | L |
| 90 | Q | F | L | S | R | V | F | T | N | S | L | V | F | G | T | S | D | R | V | Y | E | K | L | K | D | L | E | E | G | I |
| 120 | L | A | L | M | R | E | L | E | D | G | T | P | R | A | G | Q | I | L | K | Q | T | Y | D | K | F | D | T | N | M | R |
| 150 | S | D | D | A | L | L | K | N | Y | G | L | L | S | C | F | R | K | D | L | H | K | T | E | T | Y | L | R | V | M | K |
| 180 | C | R | R | F | G | E | A | S | C | A | F | * | | | | | | | | | | | | | | | | | | |

The plasmid is introduced into *E. coli*, which is cultivated under usual conditions. The formed fusion product is isolated and purified by chromatographic methods, followed by a treatment with the enzyme DAP I. The reaction mixture was processed to develop pure bGH.

EXAMPLE 9

Preparation of pickwale ribonuclease, pwR

Usual biotechnological methods are used for the preparation of a plasmid which codes for an extended protein having the formula MFEE-pwR, where the sequence pwR has the following structure:

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| 1 | R | E | S | P | A | M | K | T | Q | R | Q | H | M | D | S | G | N | S | P | G | N | N | P | N | Y | C | N | Q | M | M |
| 31 | M | R | R | K | M | T | Q | G | R | C | K | P | V | N | T | F | V | H | E | S | L | E | D | V | K | A | V | C | S | Q |
| 61 | K | N | V | L | C | K | N | G | R | T | N | C | Y | E | S | N | S | T | M | H | I | T | D | C | R | Q | T | G | S | S |
| 91 | K | Y | P | N | C | A | Y | K | T | S | Q | K | E | K | H | I | I | V | A | C | E | G | N | P | Y | V | P | V | H | F |
| 121 | D | N | S | V | * | | | | | | | | | | | | | | | | | | | | | | | | | |

The plasmid is introduced into *E. coli*, which is cultivated under usual conditions. The formed fusion product is isolated and purified chromatographically, and it is treated with the enzyme DAP I. The reaction mixture is processed to isolate pure pwR.

We claim:

1. A process for preparing ripe proteins, which comprises expressing in a procaryotic or eukaryotic cell a DNA sequence which codes for the synthesis of a fusion protein which comprises the amino acid sequence of the desired ripe protein and a N-terminal amino acid pro-sequence, cleaving the pro-sequence using DAP I and recovering the desired ripe protein.

2. The process according to claim 1 wherein the cell is a bacterial cell.

3. The process according to claim 2 wherein the bacterial cell is *E. coli*.

4. The process according to claim 1 wherein the ripe protein is a peptide hormone.

5. The process according to claim 1 wherein the desired ripe protein is human growth hormone and the pro-sequence is negatively charged.

6. The process according to claim 1 wherein the amino acid sequence of the pro-sequence is selected to facilitate purification of the fusion protein.

7. The process according to claim 1 wherein the amino acid sequence of the pro-sequence is selected so that the desired cleavage using DAP-I is facilitated.

8. The process according to claim 1 wherein the amino acid sequence of the pro-sequence is selected to facilitate transportation of the fusion protein out of the cell and extracellular cleavage by DAP-I.

9. The process according to claim 1 wherein the ripe protein has proline as the next-to-the-outermost N-terminal amino acid.

10. The process according to claim 1 in which the pro-sequence contains 2 amino acids.

11. The process according to claim 1 in which the pro-sequence is Met-Glu-Ala-Glu.

12. The process according to claim 1 in which the pro-sequence is Met-Phe-Glu-Glu.

13. The process according to claim 1 in which the pro-sequence is Met-Thr-Glu-Glu.

14. The process according to claim 1 in which the pro-sequence is Met-Glu-Glu-Glu.

15. The process according to claim 1 in which the pro-sequence is Ala-Glu-Ala-Glu.

16. The process according to claim 1 in which the initial amine acid of the pro-sequence is Met.

17. The process according to claim 1 in which the pro-sequence is Ala-Glu.

18. The process according to claim 1 in which the C-terminal amine acid of the pro-sequence is glu or Asp.

19. A process for separating a desired ripe protein from a fusion protein comprising the desired ripe protein having a negatively charged amino acid sequence of suitable length fused to the N-terminus of said desired ripe protein, said amino acid sequence comprising an even number of amino acids, which process comprises cleaving the amino acid sequence using dipeptidyl aminopeptidase I under suitable cleavage conditions, and recovering the desired ripe protein utilizing the existence of the negative charge in the amino acid sequence.

20. A process according to claim 19 wherein the amino acid sequence has an amino acid having a negative charge on the amino acid which is directly attached to the N-terminus of the ripe protein.

21. A process according to claim 19 wherein the amino acid sequence is four amino acids in length.

22. A process according to claim 19 wherein the amino acid sequence is two acid acids in length.

23. A process according to claim 19 wherein the C-terminal amino acid of the amino acid sequence is Glu or Asp.

24. A process according to claim 19 wherein the N-terminal amino acid of the amino acid sequence is Met.

25. A process according to claims 24 wherein the C-terminal amino acid of the amino acid sequence is Glu or Asp.

26. A process according to claim 19 wherein the amino acid sequence is Ala-Glu.

27. A process according to claim 19 wherein the amino acid sequence is Met-Glu-Ala-Glu.

28. A process according to claim 19 wherein the amino acid sequence is Met-Phe-Glu-Glu.

29. A process according to claim 19 wherein the amino acid sequence is Met-Thr-Glu-Glu.

30. A process according to claim 19 wherein the amino acid sequence is Met-Glu-Glu-Glu.

31. A process according to claim 19 wherein the amino acid sequence is Ala-Glu-Ala-Glu.

32. A process according to claim 19 wherein the ripe protein is human growth hormone.

33. A process according to claim 19 wherein the ripe protein is interlinear I.

34. A process according to claim 19 wherein the ripe protein is human lysozyme.

35. A process according to claim 19 wherein the ripe protein is insulin-like growth factor I.

36. A process according to claim 19 wherein the ripe protein is bovine growth hormone.

37. A process for separating a desired ripe protein from a fusion protein comprising the desired ripe protein having a charged amino acid sequence of suitable length fused to the N-terminus of said desired ripe protein wherein at least one of the charged amino acids is attached to the N-terminal of said desired ripe protein, said amino acid sequence comprising an even number of amino acids, which process comprises cleaving the amino acid sequence using dipeptidyl aminopeptidase I under suitable cleavage conditions, and recovering the desired ripe protein utilizing the existence of the charge in the charged amino acid sequence.

38. A process according to claim 37 wherein the charged amino acid sequence is either exclusively positively charged or exclusively negatively charged.

39. A process according to claim 37 wherein the charged amino acid sequence is exclusively positively charged.

40. A process according to claim 37 wherein the amino acid sequence is four amino acids in length.

41. A process according to claim 37 wherein the amino acid sequence is two amino acids in length.

42. A process for preparing a desired ripe protein which comprises expressing in a procaryotic or eukaryotic cell a DNA sequence which codes for the synthesis of a fusion protein which comprises the amino acid sequence of the desired ripe protein and an N-terminal amino acid pro-sequence, cleaving the pro-sequence using an dipeptidyl aminopeptidase and recovering the desired ripe protein.

43. A method of producing a protein consisting of amine acids 1–191 of human growth hormone comprising:
   a) expressing in a bacterial cell, DNA coding for a human growth hormone conjugate protein, which conjugate protein consists of amino acids 1–191 of human growth hormone and the additional amino acid sequence Met-Glu-Ala-Glu, and
   (b) cleaving extracellularly said conjugate protein using DAP I to produce said protein consisting of amino acid 1–191 of human growth hormone.

44. A process for producing ripe human growth hormone comprising
   (a) introducing into bacteria a recombinant DNA vector comprising a DNA sequence encoding an amino-terminal extended human growth hormone having the formula X-human growth hormone in which X is an amino acid sequence in which the N-terminal amino acid of X is different from Lys and Arg, all other uneven amino acids are different from Pro, Lys and Arg, and all even amino acids are different from Pro and in which at least one amino acid in the amino acid sequence X is a charged amino acid;
   (b) growing the bacteria such that the amino-terminal extended human growth hormone is expressed;
   (c) separating the amino-terminal extended human growth hormone in step (b) from contaminants;
   (d) cleaving the amino-terminal extension of the amino-terminal extended human growth hormone of step (c) with dipeptidyl aminopeptidase I to obtain ripe human growth hormone; and
   (e) isolating ripe human growth hormone from step (d).

* * * * *